United States Patent
Wong et al.

[11] Patent Number: 5,484,406
[45] Date of Patent: Jan. 16, 1996

[54] IN-LINE DRUG DELIVERY DEVICE FOR USE WITH A STANDARD IV ADMINISTRATION SET AND A METHOD FOR DELIVERY

[75] Inventors: Joseph Wong, Gurnee; Irwin B. Levine, Mundelein, both of Ill.

[73] Assignee: Baxter International Inc., Deerfield, Ill.

[21] Appl. No.: 168,594

[22] Filed: Dec. 16, 1993

Related U.S. Application Data

[63] Continuation-in-part of Ser. No. 978,555, Nov. 19, 1992, Pat. No. 5,385,547.

[51] Int. Cl.$^6$ ................................. A61M 37/00
[52] U.S. Cl. ..................... 604/87; 604/89; 604/408; 141/114
[58] Field of Search ................. 604/28, 49, 403, 604/404, 408–416, 201, 204, 205, 56, 82–84, 86–88, 90; 128/DIG. 24; 141/21, 23–25, 27, 114, 313, 329, 330; 222/206, 213

[56] References Cited

U.S. PATENT DOCUMENTS

| | | | |
|---|---|---|---|
| 3,610,297 | 10/1971 | Raaf et al. | 607/89 X |
| 3,788,369 | 1/1974 | Killinger | 604/408 X |
| 4,589,879 | 5/1986 | Pearson | 604/411 |
| 4,979,941 | 12/1990 | Ogle, III | 604/82 |

OTHER PUBLICATIONS

Webster's New World Dictionary, 3rd Edition (1988), p. 1005.

*Primary Examiner*—C. Fred Rosenbaum
*Assistant Examiner*—V. Alexander
*Attorney, Agent, or Firm*—Mark Buonaiuto; Paul C. Flattery; Jeffrey C. Nichols

[57] ABSTRACT

A drug delivery device (250) is provided for coupling a container (260) including a beneficial agent (262) to the device (250). The device (250) includes a substantially hollow member for housing a solution (256) wherein the hollow member includes an upper section (254) having flexible walls and a lower section (252) having substantially rigid walls. A spike (258) extends from the lower section (252) to provide fluid communication between an interior of the device (250) and the container (260). To this end, the beneficial agent (262) mixes with the solution (256) forming a mixture for administration to a patient. A cannula (266) and a plunger (264) are further provided for administration of the mixture (270) to the patient.

17 Claims, 5 Drawing Sheets

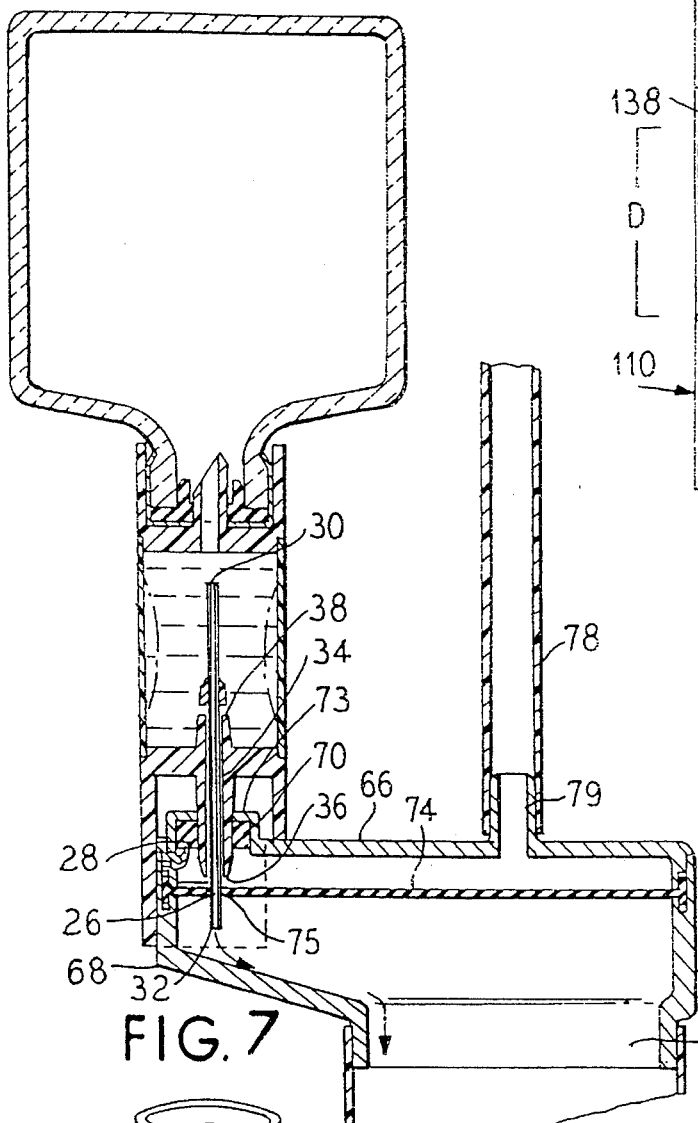
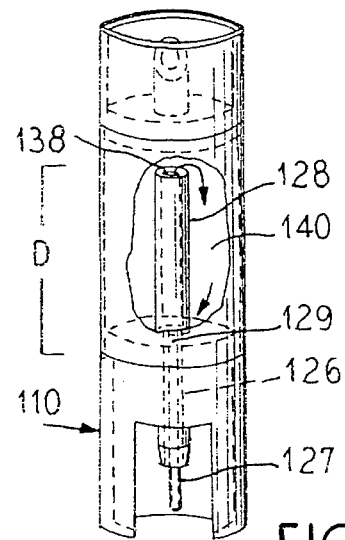
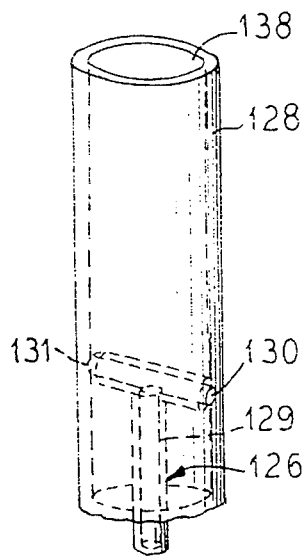
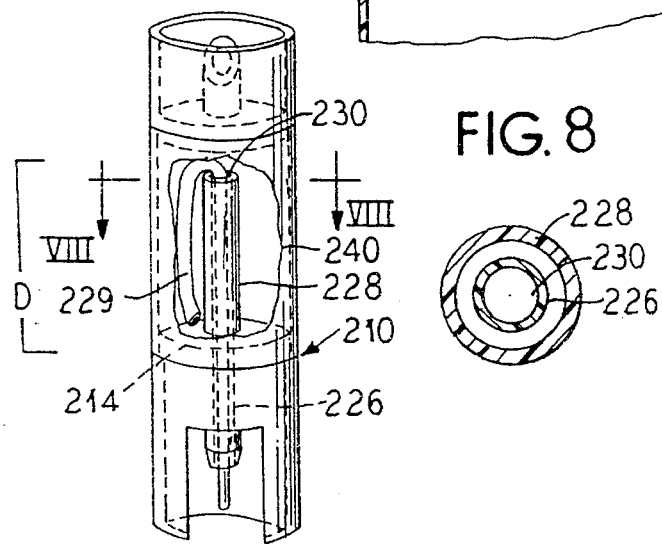
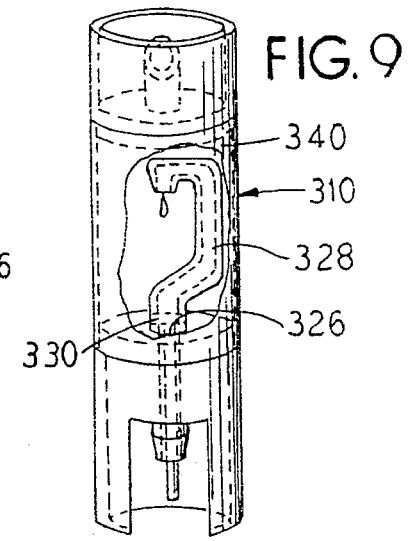

IN-LINE DRUG DELIVERY DEVICE FOR USE WITH A STANDARD IV ADMINISTRATION SET AND A METHOD FOR DELIVERY

This application is a continuation-in-part of commonly assigned U.S. patent application Ser. No. 07/978,555 filed on Nov. 19, 1992, now U.S. Pat. No. 5,385,547.

BACKGROUND OF THE INVENTION

The present invention relates generally to the delivery of a beneficial agent to a patient or into a system for later delivery to a patient. More specifically, the present invention relates to an improved drug delivery system.

For many applications, drugs can be mixed with a diluent before being delivered, for example, intravenously to a patient. The diluent can be, for example, a dextrose solution, a saline solution, or even water. To this end, many drugs are supplied in powdered form and packaged in glass vials. Other drugs, such as some chemotherapy drugs, are packaged in glass vials in a liquid state.

Powdered drugs can be reconstituted by utilizing a syringe to inject liquid into a vial for mixing; the syringe eventually withdrawing the mixed solution from the vial. When a drug must be diluted before delivery to a patient, the drug is often injected into a container of diluent after it is reconstituted; a container can be connected to an administration set for delivery to the patient.

Drugs may De packaged separate from the diluent for various reasons. One of the most important reasons is that many drugs do not retain their chemical and physical stability when mixed with a diluent and thus cannot be stored for any substantial period of time. Also, drugs are often packaged separately from the diluent because many companies that manufacture drugs are not engaged in the business of providing medical fluids and containers for intravenous delivery, and vice versa.

Therefore, doctors, nurses, pharmacists, or other medical personnel must mix the drug and diluent. This presents a number of problems. The reconstitution procedure is time consuming and requires aseptic techniques. The operator must provide the proper diluent and a syringe before beginning. The reconstitution procedure should be performed under preferably sterile conditions. This procedure requires the operator to be more cautious, thereby consuming more time. Additionally, sterile conditions are often hard to maintain. In some instances, a laminar flow hood may be required under which the reconstitution procedure is performed.

A further concern is that some drugs, such as chemotherapy drugs, are toxic. Exposure of the operator to the drugs during reconstitution can be dangerous, especially if the operator works with such drugs on a daily basis and is repeatedly exposed to them.

Although after a drug is reconstituted and withdrawn into a syringe barrel, the drug can, in some instances, be injected immediately into a patient. More typically, however, the reconstituted drug is injected from the syringe into a larger container of solution for connection to an intravenous administration set. A larger container of solution may be necessary because often the reconstituted drug in the syringe is at such a concentration as to cause local toxicity in the veins of a patient near the injection site where the needle pierces the skin. This can create severe vein irritation which can be harmful.

Additionally, even though the proper dose of medication may be in the syringe, immediate injection into the blood stream of a patient can create a condition of systemic toxicity wherein the level of drug concentration in the entire blood system of the patient is dangerously high. Yet another reason for not making an injection from the syringe directly into the patient is that such an injection creates an additional injection site into the patient; this can be painful for the patient and provides another opportunity for infection.

For these reasons, the reconstituted drug is more typically injected into a diluent container.

A number of drug delivery systems are known. In one delivery system that is currently used, a drug contained in a vial in a solid state is reconstituted with a predetermined volume of diluent using a needle and syringe. The vial containing the drug and solution is then mated onto an intravenous administration set. The drug is delivered to a patient as diluent flows through the vial to the patient carrying with it the dissolved drug.

In another IV drug delivery system, the drug solution is packaged in flexible plastic containers. Some drugs packaged in this manner may be stored at room temperature, and the drug is delivered by connecting the container to an intravenous administration set. Some drugs packaged in this manner may be stored in a frozen state in order to improve drug stability. In these cases, the drug solution must be thawed and then connected to an intravenous administration set for delivery to the patient.

Another system requires drugs to be contained in a special vial. An activated vial is then mated to a special container. The vial stopper is removed, and the drug is transferred to the container by flushing the vial with the diluent in the container. The drug is delivered by connecting the container with the dissolved drug to an intravenous administration set.

Drugs can also be delivered intravenously via a syringe pump. Briefly, a dose of reconstituted drug solution is withdrawn by a syringe. The drug solution in the syringe is then refrigerated or frozen until use. The drug solution is brought to room temperature and infused into a patient via a syringe pump.

There are some disadvantages with some of the above systems and procedures. One of the disadvantages is drug waste. Due to chemical and physical instability, once a solid drug is reconstituted with diluent (or a frozen formulation is thawed), it cannot be stored for any substantial amount of time. Therefore, if the drug solution is not, administered to the patient within a given period of time, the drug must be discarded. Drug waste can be a very costly expense to a hospital pharmacy.

Some of the current procedures for intravenous administration are labor intensive. As previously noted, reconstitution of a drug with a needle and syringe is time consuming and requires an aseptic environment. Likewise, exposure of the operator to the drug may be dangerous, especially if the operator works with the drug on a daily basis. Of course, needle sticks may expose healthcare professionals to hazardous diseases and infections.

A further disadvantage of some of the above procedures is hat they require a secondary IV administration set for delivery of the drug. The secondary set can be cumbersome for both the patient and the clinician. Elimination of the secondary set (along with the needle and syringe) may also reduce solid waste and disposal costs.

U.S. Pat. No. 4,850,978 discloses a drug delivery system for delivering drugs to patients and/or reconstitution of a drug. The system includes a cartridge for introducing a beneficial agent into a fluid conduit for delivery of the agent to a patient. The cartridge includes a rigid hollow tube and an agent containing chamber slidably mounted at least partially within the hollow tube. In a first, pre-use position, the chamber extends farther from the hollow tube than it does in a second position. A cannula is mounted to the hollow tube extending opposite the chamber. When the chamber is in the second position, the cannula pierces the closure means creating a flow path.

U.S. Pat. No. 4,804,366 also discloses a drug delivery system including an adapter having an improved flow path means providing both an inlet and an outlet to the agent containing chamber of a cartridge. The cartridge and adapter permit a single opening through the injection sites at opposite ends of the flow path means, while still permitting simultaneous flow both into and out of the chamber. An adapter and a cartridge is provided, including a rigid cannula with an inlet and an outlet and the shell substantially coaxial with and spaced from the cannula intermediate of the cannula inlet and the cannula outlet so that the shell of the cannula defines a channel therebetween. Both the cannula inlet and the cannula outlet are adaptable to form a single piercing opening in a resilient injection site associated with the cartridge.

SUMMARY OF THE INVENTION

The present invention provides a simplified apparatus and method for the reconstitution or mixture of a drug and a diluent. The present invention further provides an improved administration procedure for delivery of a drug to a patient. More specifically, the present invention provides a system and method for mixing a unit dosage of a beneficial agent contained within a vial with a solution contained within a syringe for administration of a unit dose to a patient.

To this end, in an embodiment, a device is provided for mixing a solution with a beneficial agent in a container forming a mixture for further administration. The device comprises a substantially hollow member having an interior containing the solution and further having an upper section and a lower section wherein the upper section includes walls that at least partially define an exterior of the upper section that are capable of, at least in part, being biased inwardly thereby exerting a pressure on the solution contained within the hollow member. A means for piercing is constructed and arranged to provide fluid communication between an interior of the substantially hollow member at the lower section and the container. A port is constructed and arranged for coupling a cannula thereto, the cannula providing fluid communication with the interior of the hollow member.

In an embodiment, the walls of the upper section are at least partially flexible.

In an embodiment, the lower section is defined by substantially rigid exterior walls.

In an embodiment, the means for piercing extends perpendicularly to a length of the hollow member.

In an embodiment, the solution within the hollow member mixes with the beneficial agent to form an individual unit dosage for administration to a patient.

The present invention further provides a method for mixing a beneficial agent housed in a first container with a solution housed in a second container forming a mixture for administration thereof. The method comprises the steps of: providing a means for piercing constructed and arranged to provide selective fluid communication between the first container and the second container; coupling the second container to the first container with the means for piercing; compressing at least a portion of an exterior of the second container forcing the solution from the second container into the first container; mixing the solution and the beneficial agent; and releasing compression on the portion of the exterior of the second container allowing the mixture to return to the second container.

In an embodiment, at least a portion of the exterior of the second container includes rigid walls.

In an embodiment, only a portion of the solution is compressed from the second container into the first container.

The present invention further provides a method for drug delivery. The method comprises the steps of: providing a device having an interior for housing a solution, the device further having an upper section with flexible walls and a lower section; coupling a container having an interior containing a beneficial agent to the lower section of the device; establishing fluid communication between the interior of the container and the lower section of the device; compressing a portion of the flexible walls defining the upper section to cause the solution to flow into the container; releasing compression of the portion of the wall allowing a mixture of the solution and the beneficial agent to return to the interior of the device; and coupling a means for administering the mixture in the device to a patient.

In an embodiment, the container is a vial having a re-sealable injection site.

It is, therefore, an advantage of the present invention to provide a device for simplified reconstitution of a beneficial agent and a solution.

Another advantage of the present invention is to provide a device that allows, for example, an end-user to simply reconstitute the beneficial agent with the solution.

Still further, an advantage of the present invention is to reduce the risk of injury from, for example, needle sticks.

Moreover, an advantage of the present invention is to reduce material waste.

And further, an advantage of the present invention is to reduce the likelihood of medication error.

Yet another advantage of the present invention is to reduce storage space required for drug typically administered to patients.

Additionally, an advantage of the present invention is to reduce the likelihood of contamination to a drug mixing and delivery system.

Furthermore, an advantage of the present invention is to provide a system for drug delivery wherein the components for drug delivery and the drug itself can be stored at room temperature.

Still further, an advantage of the present invention is to provide a pre-measured diluent within a device for mixture with a beneficial agent.

Additional features and advantages of the present invention are described in, and will be apparent from, the detailed description of the presently preferred embodiments and from the drawings.

BRIEF DESCRIPTION OF THE DRAWINGS

FIG. 4 illustrates the vial and adaptor arrangement of FIG. 2 mated to an infusion set.

FIG. 5 illustrates an embodiment of the adaptor of the present invention.

FIG. 6 illustrates an enlarged perspective view of the flow paths of the embodiment of FIG. 5 with parts broken away.

FIG. 7 illustrates a further embodiment of the adaptor of the present invention.

FIG. 8 illustrates a cross-sectional view of the cannula of the adaptor of FIG. 7 taken along lines VIII—VIII.

FIG. 9 illustrates still a further embodiment of the adaptor of the present invention.

DETAILED DESCRIPTION OF THE PRESENTLY PREFERRED EMBODIMENTS

The present invention provides an apparatus for delivering a beneficial agent to a patient. Additionally, the present invention provides improved methods for administering a drug to a patient. Furthermore, the present invention provides an in-line drug delivery device for administering a drug to a patient using any standard intravenous administration set. As set forth in detail hereinafter, due to the construction of the apparatus of the present invention, it can be utilized with most any intravenous drug. To this end, for example, the apparatus can be modified to provide drug delivery profiles allowing the administration of many varied drugs.

Figure 1:
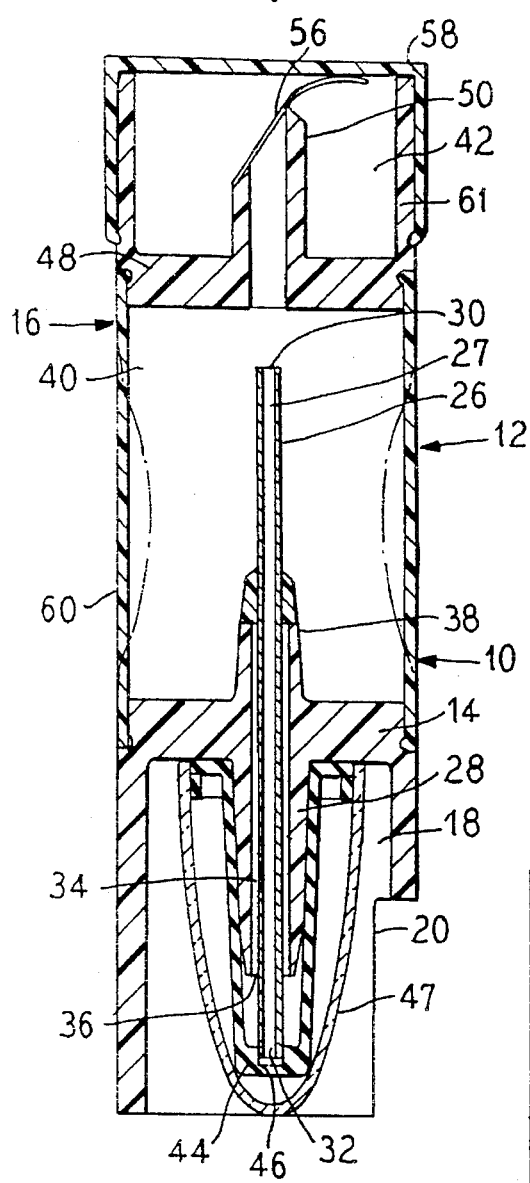
FIG. 1 illustrates a perspective view of an embodiment of the adaptor of the present invention.

Referring now to FIG. 1, an embodiment of the adaptor 10 is illustrated, As illustrated, the adaptor 10 preferably comprises a substantially tubular-shaped cartridge 12 that is divided by a wall 14 into an upper section 16 and a lower section 18. The lower section 18 comprising a substantially rigid member having a key wall 20. The wall 14 is mounted across the cartridge 12 and defines the staring point for the key wall 20.

In the preferred embodiment illustrated, a cannula 26 extends through the wall 14. The cannula 26 defines a channel 27. Additionally, a generally cylindrical shell 28 extends from both sides of the wall 14.

The shell 28 is spaced from the cannula 26 with the shell, in the embodiment illustrated in FIG. 1, encompassing the cannula but being shorter at either end of the cannula. The cannula 26 includes an inlet and an outlet 30 and 32, respectively. Preferably, the inlet and the outlet 0 and 32 of the cannula 26 are blunt. Of course, if desired, either or both of these members could be pointed.

The shell 28 is intermediate of the cannula inlet and outlet 30 and 32. The cannula 26 and shell 28 define a second channel 34 therebetween. In a preferred embodiment, the periphery of the cannula 26 is circular along its length. Similarly, the internal surface of the shell 28 is preferably arcuate and preferably circular along its length.

The second channel 34 includes a channel inlet 36 defined between the shell 28 and the cannula 26, short of the cannula outlet 32. Similarly, the second channel includes a channel outlet 38 defined by the shell 28 and the cannula 26, short of the cannula inlet 30.

The cannula 26 is secured to the shell 28 while still maintaining an open flow path through the channel inlet 36, the channel 34, and the channel outlet 38. Thus, a very small flow path is created outside a single cannula with precision.

Figure 2:
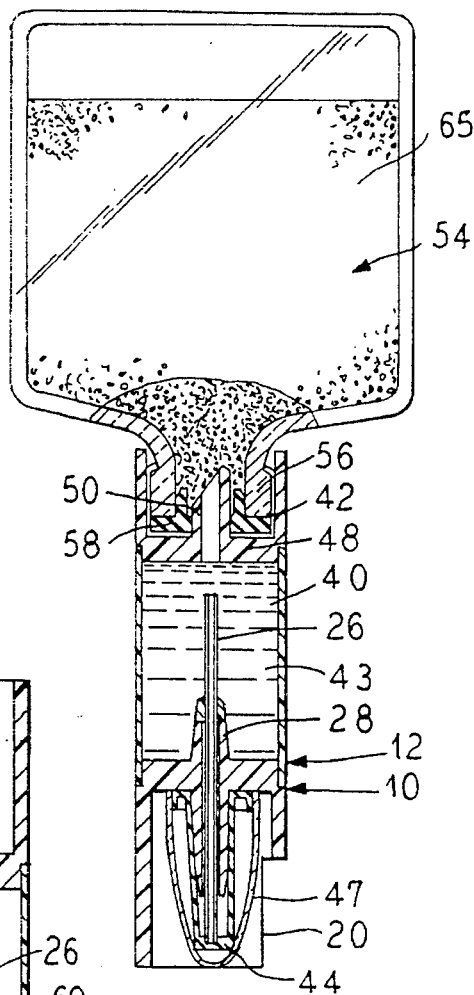
FIG. 2 illustrates an embodiment of the adaptor of the present invention wherein a vial has been mated to the adaptor.

The upper section 16 of the cartridge 12 is designed to preferably receive a diluent. To this end, in the preferred embodiment illustrated, the upper section 16 includes a first and second section 40 and 42, respectively. As illustrated in FIG. 2, the first section 40 is designed to house the diluent 43.

In order to prevent the diluent from flowing from the first section 40 out through the channels 27 and 34, as illustrated in FIG. 1 a sheath 44 is provided for covering the end of the cannula and shell 28. Preferably, the sheath 44 is substantially similar to that disclosed in U.S. Pat. No. 5,167,642 entitled: "SHEATH FOR CANNULA", the disclosure of which is incorporated herein by reference. As set forth in that patent application, the sheath 44 provides a watertight seal thereby preventing any of the diluent from leaking out of either of the channels defined by the cannula 26 or shell 28.

However, the sheath 44 is also so constructed and arranged that even when used with a blunt ended cannula 26, the sheath will rip, not core, upon the exertion of a sufficient force by the blunt end of the cannula against the walls 46. This allows the blunt end of the cannula 26 to be received within an injection site without first having to manually remove the sheath 44. The sheath 44 will fold back along the cannula 26 and the shell 28 in an accordion fashion. This will allow the blunt end of the cannula 26 and shell 28 to enter the injection site, but prevent the sheath 44 from entering the injection site.

Due to the use of the sheath, the entire first section 40 of the adaptor 12 can be filled with diluent if desired. Additionally, if desired, a removable cover 47 can be provided to protect the sheath 44 prior to use of the cartridge.

To divide the upper section 16 into first and second sections 40 and 42, a wall 48 is provided. Preferably, the wall 48 includes means for piercing a vial. In the preferred embodiment illustrated, the wall 58 includes a spike 50 that provides fluid communication between the first and second sections 40 and 42. The wall 48 prevents diluent housed in the adaptor 10 from leaking out of a top of the first section 40 of the adaptor 10.

The spike 50 provides means for providing fluid communication between the first section 40 of the adaptor 10 and a vial 54 to be docketed on the second section 42 of the adaptor. Of course, any piercing means that allows fluid flow between the vial 54 and the adaptor 10 can be used. As illustrated, preferably, the spike 50 includes a foil seal 56 to prevent leakage of the diluent prior to docking with a vial 54.

Additionally, to insure the sterility of the spike 50, a removable cover 58 can be provided.

In the preferred embodiment illustrated, the spike 50 is located so as to be recessed from a plane defined by an open end of the second section 42. Because the spike 50 is recessed, this acts to reduce accidental "sticks" of personnel handling the adaptor 10 as well as prevent touch contamination.

If desired, the second section 42 can include on an interior surface bumps (not shown) having a sloped side facing the open end of the second section. Such a structure assists in securing a vial 54 to the adaptor 10. An example of such a structure is set forth in PCT Published Application No. WO91/11152, the disclosure of which is hereby incorporated herein by reference.

As illustrated in FIG. 2, in use, a vial 54 is mated with the adaptor 10. To this end, at least the top portion 56 of the vial 54 is received in the second section 42 of the adaptor 10. This causes the spike 50 to pierce a rubber stopper 58 of the vial 54, establishing fluid communication between the cartridge 12 and the vial 54. Due to the construction of the cartridge 12, the cartridge can mate with any standard off-the-shelf vial 54 containing a beneficial agent.

Pursuant to the present invention, at least a portion of the walls 60 that define the first section 40 can be biased inwardly, as illustrated in phantom lines in FIG. 1. Preferably, at least a portion of the walls 60 are constructed from a flexible material. The material, however, should be sufficiently rigid to provide stability to the adaptor 10, but allow the walls 60 to be biased inward. In a preferred embodiment, the entire walls 60 are flexible. Conversely, the walls 61 that define the upper section 40, if desired, can be rigid.

Figure 3:
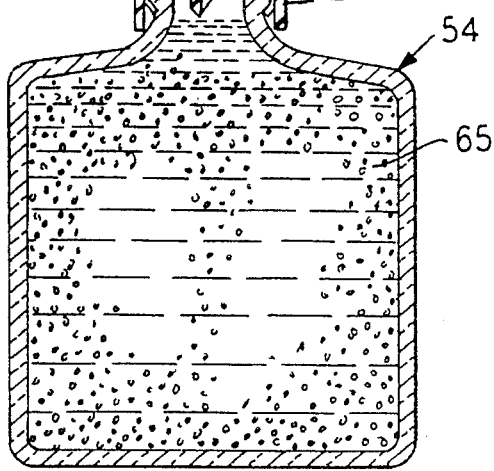
FIG. 3 illustrates a perspective view of the adaptor and vial arrangement of FIG. 2 wherein diluent from the adaptor has been added to the vial.

As illustrated in FIG. 3, in order to reconstitute or dilute a drug 65 contained in the vial 54, the adaptor 10 is turned upside down. Diluent 43 contained in the adaptor 10 is then forced into the vial 54 by squeezing the flexible walls 60 of the adaptor. This forces the diluent 62 from the adaptor 10 into the interior of the mated drug vial 54.

The drug 65 contained within the vial 54 is then allowed to dissolve and/or mix with the diluent. The resultant drug solution is then transferred back into the adaptor 10 by holding the adaptor in an upright position such that the solution is at the stopper end of the vial 54. The adaptor 10 is then compressed forcing air into the vial 54. The higher pressure in the vial 54 then forces the liquid from the vial into the adaptor 10.

Referring now to FIG. 4, the adaptor 10 can then connected to an IV administration set, for example, the MAINSTREAM™ administration set available from Baxter Healthcare of Deerfield, Ill. The drug that was contained in the vial 54 can now be delivered to the patient. To accomplish this, the adaptor 10 is docketed on a receptacle 64. The receptacle 64 includes upper and lower fitments 66 and 68. The upper fitment 66 includes an inlet 70. The lower fitment 68 includes the outlet 72. A pierceable resealable injection site 73 is mounted within the upper fitment 66 of the receptacle 64. An example of such an IV administration set is disclosed in U.S. Pat. No. 4,804,366, the disclosure of which is incorporated herein by reference.

The receptacle 64 includes a resilient divider 74 trapped between the upper and lower fitments 66 and 68 of the receptacle 64. The resilient divider 74 defines a narrow through bore 75 directly below the resilient pierceable injection site 70. Before the cartridge 10 of the present invention is engaged with the receptacle 64, fluid flowing from a parenteral container 76 flows through the fluid conduit 78 and through a receptacle inlet 79 whereon it flows into the receptacle above the dividing plate 74, through the through bore 75 and downstream to the receptacle outlet 72. Fluid then flows downstream to the patient.

As illustrated in FIG. 4, when the cartridge 12 is mounted on the receptacle 64 the cannula 26 and the shell 28 pierce the resilient injection site 70. The cartridge 12 continues to be urged downwardly so that the cannula outlet 32 enters the through bore 75 and is liquid-sealingly engaged by the resilient divider 74 around the periphery of the cannula outlet 32.

Upon engagement of the cartridge 10 and receptacle 64, as illustrated in FIG. 4, liquid flowing into the receptacle at the inlet 79 is prevented from passing through the through bore 75 and the receptacle because the resilient divider 74 has been sealed about the cannula outlet 32 portion at the through bore 75. Thus, liquid entering the receptacle enters the channel inlet 36, flows through the channel 34, and enters the first section 40 at the channel outlet 38.

In an embodiment, as liquid rises within the first section 40, it will continue to rise until it reaches the cannula inlet 30, whereupon liquid begins to exit the chamber through the cannula 26 downstream through the cannula outlet 32. Liquid exiting the cannula 26 has an appropriate concentration for the beneficial agent mixed therewith for delivery to the patient. In the illustrated embodiment, the upward liquid flow path created within the first section 40 by the shell 28, channel 34, and cannula 26 creates a density gradient within the first section 40 such that the concentration of drug within the liquid exiting at the cannula outlet 32 will not be so high as to create local toxicity of the patient.

As illustrated in the Figures, many embodiments of the adaptor 12 are possible. The drug delivery to the patient must meet clinical guidelines. For IV therapy, these guidelines may include parameters such as delivery rate, delivery volume, and delivery concentration. Typically, the clinical guidelines for drug delivery specify a range in which the drug delivery parameters should lie. Drug delivery rates, concentrations, and volumes can be controlled by modification of the adaptor 10.

The geometry of the adaptor 10, diluent flow path, drug solution density, and drug solution volume all can be tailored to yield a desired drug delivery profile for a particular drug. Adaptor 10 design modifications can yield drug delivery rates which range from bolus IV injection to IV drip infusion.

The density of the drug solution relative to that of the diluent has a major impact on the rate of drug delivery from the adaptor 10. For a given adaptor design, the relative density of the diluent and drug solution determine the mixing characteristics in the adaptor 10 during delivery to the administration set. The adaptor 10 may be designed so that by varying only the relative density of the drug solution and diluent, the delivery rate from the adaptor can range from bolus IV to injection to IV drip infusion.

Drug delivery rates, volumes (volume required to deliver the dose), and concentrations are functions of the volume of solution in the adaptor 10. Therefore, by controlling the solution volume in the adaptor 10 drug delivery to the patient can be governed.

The drug delivery rate, volume, and maximum effluent concentration from a well stirred vessel can be expressed as:

Delivery rate: $dD/dt = D\, F/V$

Delivery volume: $L = -V \ln(D/D_o)$

Maximum effluent concentration: $M = D_o/V$

D: amount of drug in the adaptor $D_o$: initial amount of drug in the adaptor t: time F: diluent flow rate V: volume of solution in the adaptor The drug delivery rate, volume, and maximum effluent concentration from a vessel exhibiting plug flow can be expressed as:

Delivery rate: $dD/dt = F\, D_o/V$

Delivery volume: $L = V\,(D_o - D)D_o$

Maximum effluent concentration: $M = D_o/V$

D: amount of drug in the adaptor $D_o$: initial amount of drug in the adaptor t: time F: diluent flow rate V: volume of solution in the adaptor The above expressions for rate of delivery from the two vessel types show that the delivery rate is directly proportional to the flow rate and inversely proportional to the volume of solution in the vessel. Therefore, as the mixing in the adaptor 10 approaches either of the two ideal systems described, by adjusting the volume of the solution in the adaptor, the delivery rate to the administration set can be governed.

The above expressions also indicate that the delivery volume is directly proportional to the volume of solution in the adaptor 10; and the maximum effluent concentration is inversely proportional to the solution volume in the adaptor. Therefore, as the mixing in the adaptor 10 approaches either of the two ideal systems described, both parameters for a given drug can be controlled by adjusting the solution volume in the adaptor.

The internal geometry of the adaptor 10 can be designed to effect mixing of the diluent and drug solution in the adaptor 10 which will consequently affect the rate of drug delivery from the adaptor 10 to the administration set. The fluid path of the adaptor 10 can be designed to affect the mixing and consequently the delivery kinetics from the adaptor. By changing the positions of the fluid inlet and outlet, the mixing of the adaptor 10 for a given drug solution can range from approximately plug flow to approximating a well-stirred vessel.

Referring now to FIGS. 5 and 6, an embodiment of the fluid path within the adaptor is illustrated. In the illustrated embodiment, the fluid path of the adaptor 10 illustrated in FIGS. 1 and 4 is modified. To this end, the fluid flow paths in the lower section 118 of the embodiment of FIGS. 5 and 6 are substantially similar to that of the sleeve and cannula illustrated in FIGS. 1–4. However, the fluid flow paths of the fluid outlet within the first section 140 are modified.

To this end, in the embodiment of the adaptor 110 illustrated in FIG. 5, instead of a cannula structure that extends into the first section 140, a T-shaped fluid flow path 126 is provided. The fluid flow path 126 includes a lower cannula structure 127 but includes an upper T-shaped structure 129. Fluid flow out of the first section 140, as illustrated in FIGS. 5 and 6, is through two openings 130 and 131 of the T-shaped structure 126.

Instead of the shell structure 28 of FIGS. 1–4, fluid flows into the first section 140 through an extended flow path 128. The extended flow path includes an outlet 138 located near a top of the first section 140. This creates a fluid flow within the first section 140 illustrated in FIG. 5.

Accordingly the fluid inlet, with respect to the first section, is distal and the fluid outlet is proximal relative to the docking site. The distance D can be modified to yield optimal drug delivery parameters for a given drug.

FIGS. 7 and 8 illustrate another embodiment of the adaptor 210. In this embodiment, the cannula 226 and shell 228 extend for substantially the same distance into the first section 240. However, a tube 229 is connected to the inlet 230 of the cannula 226 allowing the fluid outlet path to be modified within the first section 240.

In the illustrated embodiment, the tube 229 and thereby fluid outlet path is positioned near the wall 214 at a bottom of the first section 240. In this version, again, the fluid inlet, into the first section 240, is distal and the fluid outlet is proximal relative to the docking site. The distance D can be modified to yield optimal drug delivery parameters for a given drug.

FIG. 9 illustrates a further embodiment of the adaptor 310 present invention. In this embodiment, again, the fluid outlet path 326 is defined by a T-shaped member. The fluid inlet path is defined by an extended member 328 that extends near a top of the first section 340.

The fluid inlet 338 is therefore distal and the outlet 330 proximal to the docking site. The inlet 338 is positioned above the solution levels. The fluid inlet 338 is constructed so that it creates droplets of fluid accordingly, as diluent enters the adaptor 310, it drops into the solution. The drops of diluent falling into the adaptor solution will increase the mixing in the adaptor 310. The location of the fluid outlet can be modified so as to optimize drug delivery for a given drug.

In an embodiment, it is possible for the adaptor 10 to be designed to contain drug in a liquid state within the first section 40. The drug formulation can thereby be stored in the adaptor body. A site for vial 54 access therefore would not be necessary.

If desired, the fluid, drug or diluent, can be a frozen solution stored in the adaptor 10. The solution then being thawed and the adaptor 10 docketed to the MAIN-STREAM™ access site.

Figure 10:
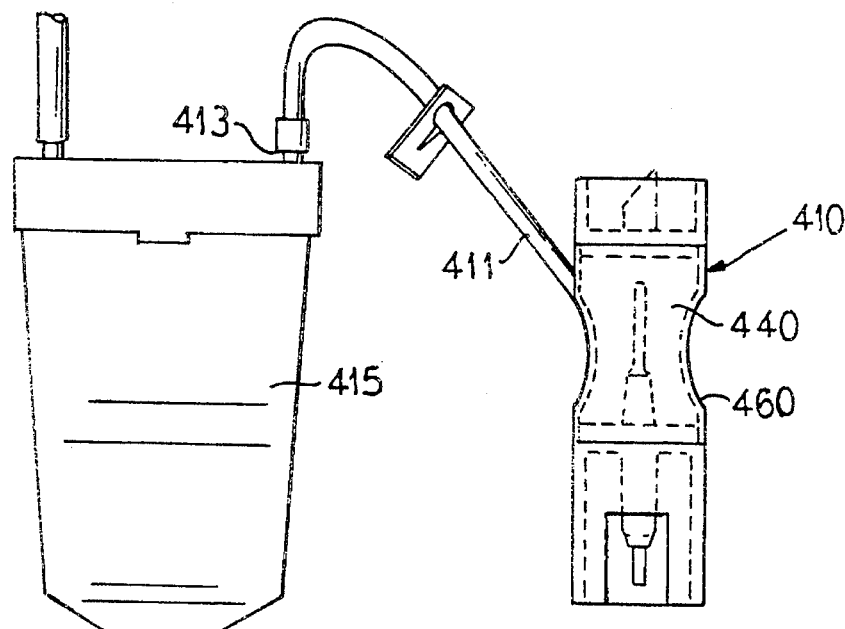
FIGS. 10–12 illustrate perspective views of an embodiment of the present invention illustrating a method for filling the adaptor with a diluent.
Figure 11:
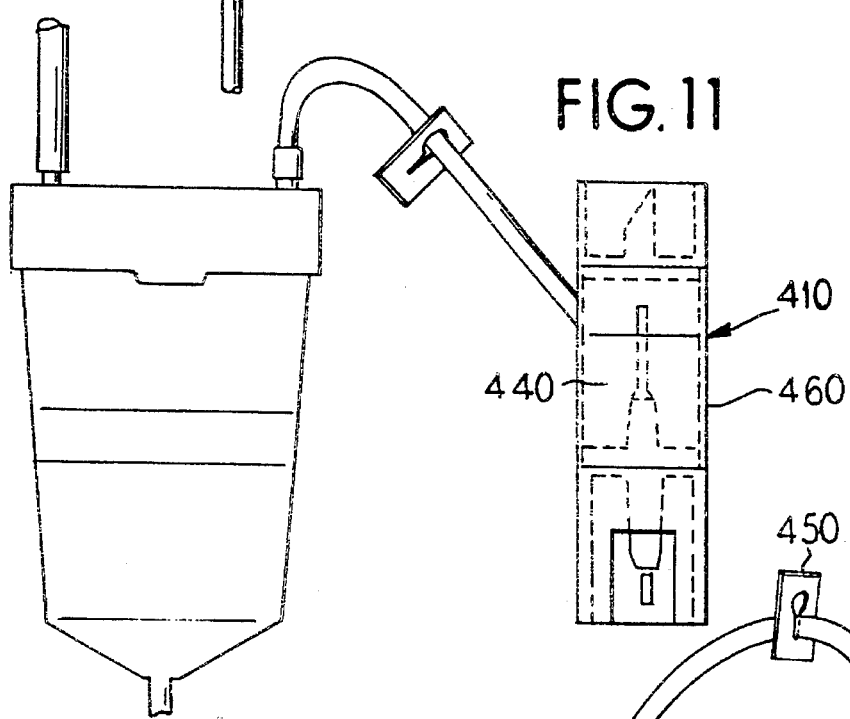
Figure 12:
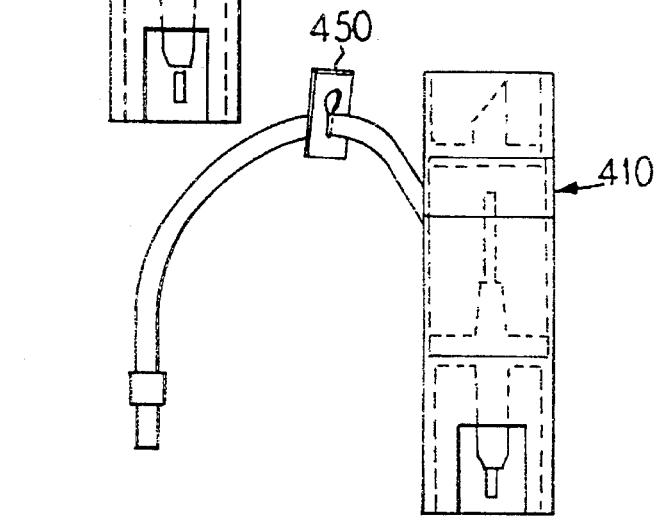
Figure 13:
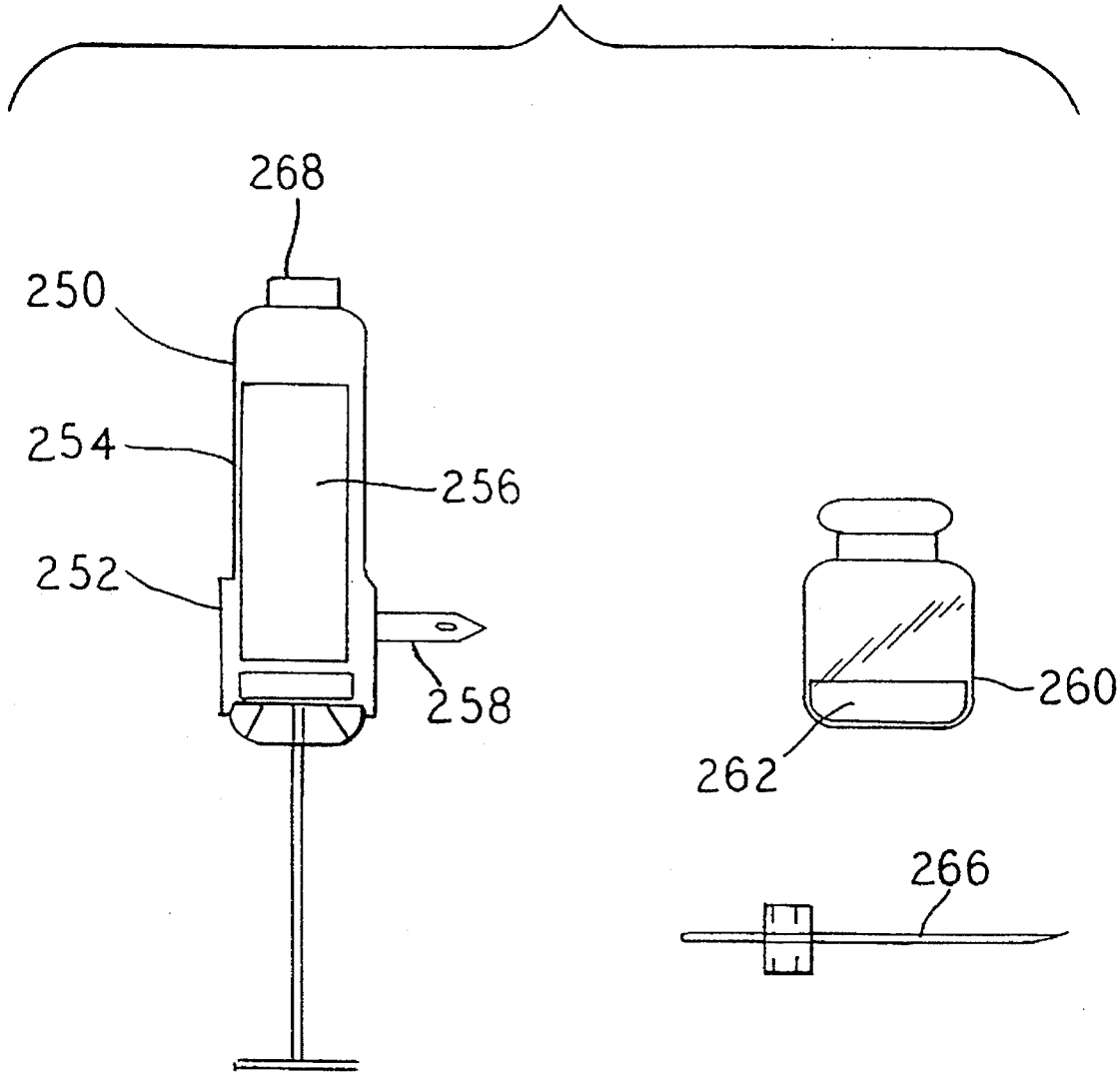
FIG. 13 illustrates a cross-sectional view of the components of another embodiment of a syringe for drug delivery of the present invention.

Although the adaptor 10 in a preferred embodiment, is provided to the end user containing diluent, the adaptor may be provided to the end user without diluent. As illustrated in FIGS. 10–12, a method for filling the adaptor 410 with diluent is illustrated.

In the illustrated embodiment, the adaptor 410 includes a conduit 411 that is in fluid communication with the first section 440. The operator plugs the conduit 411 from the adaptor 410 into an access site 413 of an IV container 415. This can be the IV container that is used to administer the drug to the patient in the IV administration set. The operator then squeezes the flexible chamber 460 of the adaptor body 410 expelling air into the IV container 415, as illustrated in FIG. 10.

Referring now to FIG. 11, by releasing the walls 460 of the adaptor 410, diluent 421 will be drawn into the adaptor 410. As illustrated in FIG. 12, after the desired amount of diluent is transferred into the adaptor 410, the conduit 411 would be clamped off, using a clamp 450 or other means, and the adaptor used as described above.

Of course, a variety of other means can be used for filling the adaptor.

Referring now to FIGS. 13–17, another embodiment of the present invention is illustrated for reconstitution and administration of drugs within a unit dose vial. To this end, a syringe 250 is provided. The syringe 250 has a rigid housing 252 at or near a base thereof. Between the housing 252 and a point, such as a port 268, at which a cannula 266 is attached is a flexible housing 254.

The rigid housing 25.2 and the flexible housing 254 preferably integrally form a single housing for containing therein a diluent as generally illustrated at 256. The diluent may be a solution such as a dextrose solution, a saline solution, water or the like.

Fluid communication can be provided with the diluent 256 within the syringe 250 by a spike 258. The spike 258 is preferably mounted at a point about the periphery of the rigid housing 252 of the syringe 250. The spike 258 acts as a port through which the solution may first exit into an attached vial or other like container, such as the vial generally illustrated at 260 in FIG. 13.

A drug 262 is provided in the vial 260 which requires mixing with the diluent 256 prior to being delivered, for example, intravenously to a patient or otherwise connected to a fluid line or other container. The syringe 250 further includes a plunger 264 for administration of the mixed drug solution to the patient following attachment of a needle or a cannula 266 to the port 268 opposite the plunger 264.

Figure 14:
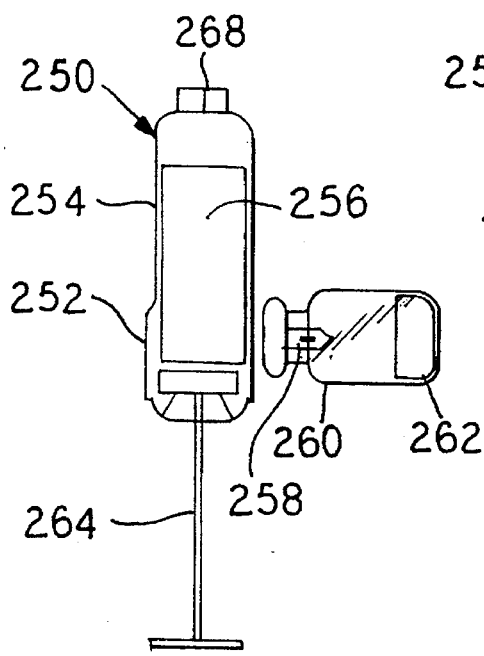
FIGS. 14 illustrates a cross-sectional view of a first step for mixing a diluent and drug with the syringe and vial of the present invention.

FIGS. 14–17 generally illustrate the steps required for mixing the diluent 256 within the syringe 250 with the drug 262 within the vial 260. First, the vial 260 is connected to the spike 258 as illustrated in FIG. 14. Following connection, the interior of the vial 260 is in fluid communication with the interior of the syringe 250 containing the diluent 256.

Figure 15:
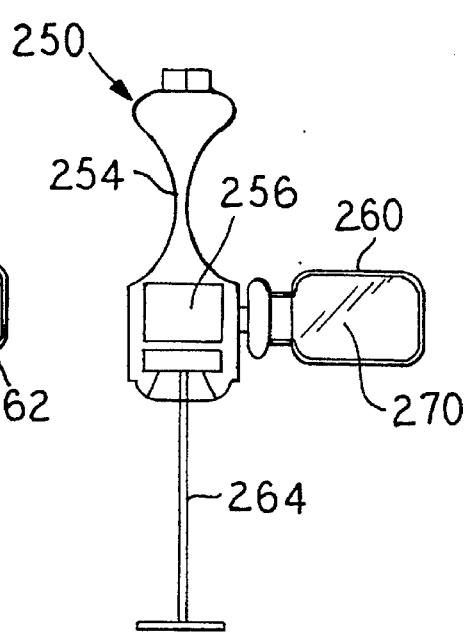
FIG. 15 illustrates a cross-sectional view of a second step for mixing a diluent and a drug with the syringe and the vial of the present invention.

Following attachment of the vial 260 to the syringe 250, the flexible housing 254 of the syringe 250 may be compressed as illustrated in FIG. 15. Compression thereof forces the diluent 256 from the interior of the syringe 250, through the spike 258, and into the interior of the vial 260. The drug 262 within the vial 260 mixes with the diluent 256 forming a drug solution 270.

Figure 16:
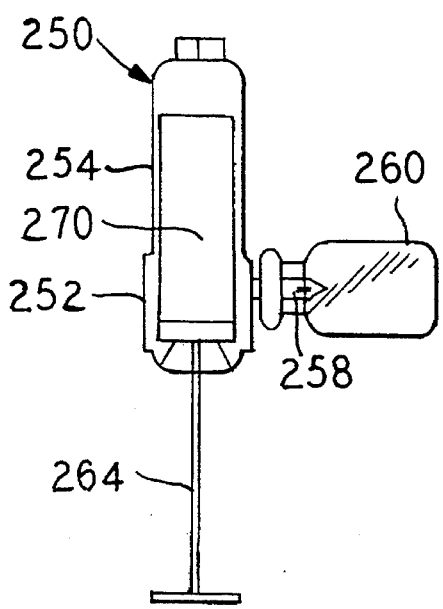
FIG. 16 illustrates a cross-sectional view of a third step for mixing the diluent and the drug with the adaptor and the vial of the present invention.
Figure 17:
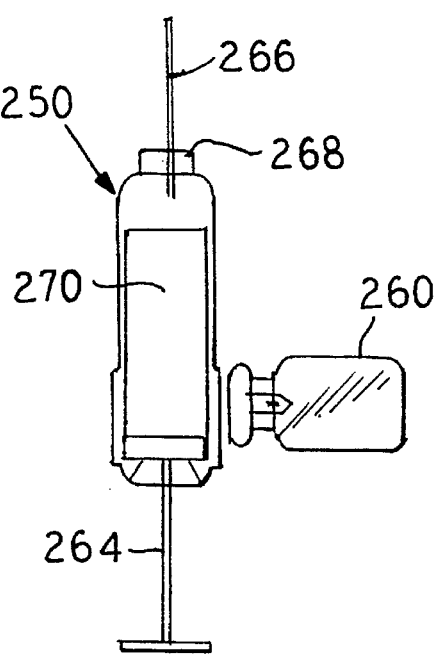
FIG. 17 illustrates a cross-sectional view of a final step prior to administering the mixed drug and diluent to a patient or other container using the syringe of the present invention.

Referring to FIG. 16, the drug solution 270 can then be transferred into the interior of the syringe 250 by releasing the compression on the flexible housing 254. The drug solution 270, therefore, passes through the spike 258 from the vial 260 into the interior of the syringe 250.

Finally, the needle or cannula 266 may be connected to the port 268 of the syringe 250 to provide fluid communication with the interior of the syringe 250. The vial 260 may be removed from the spike 258 prior to administration of the drug solution 270 to, for example, a patient, a fluid line, or other container. Alternatively, the vial 260 may remain attached as illustrated during administration of the drug solution 270 to the patient.

Preferably, the vial 260 is a unit dose-type vial, but other sizes may be implemented as required for the particular application. The diluent 256 within the syringe 250 can be pre-measured for particular amounts of a particular drug 262 within the drug vial 260. As a result, less material waste and a reduced possibility of medication error exists. Furthermore, less storage space is required, and the risk of microbial contamination is reduced. Still further, all of the components and the drug can be stored at room temperature, or, in the alternative, frozen pre-mixed drug solutions and small diluent volumes may also be implemented using the present invention as described with reference to FIGS. 13–17.

As a result of the foregoing description of the embodiment of the invention illustrated in FIGS. 13–17, the device and the method simplifies reconstitution as compared to current devices and methods for drug preparation. The end-users are only required to activate the vial and force or compress the diluent into the drug vial for reconstitution.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A device for mixing a solution with a beneficial agent in a container thereby forming a mixture for further administration, the device comprising:

a substantially hollow member having a length and an interior containing a solution and further having walls that at least partially define an exterior of the hollow member and are capable of, at least in part, being biased inwardly thereby exerting a pressure on the solution contained within the hollow member, the length of the hollow member being greater than the width;

means for piercing constructed and arranged substantially perpendicularly to the length of the hollow member and integrally connected to and extending from a wall of the hollow member wherein the means for piercing provides fluid communication between the interior of the substantially hollow member at a lower section of the hollow member and the container; and a port constructed and arranged at an end of the hollow member opposite the lower section, the port providing access to the interior of the hollow member.

2. The device of claim 1 wherein portions of the walls are flexible.

3. The device of claim 1 wherein the lower section is defined by substantially rigid exterior walls.

4. The device of claim 1 wherein the solution is a diluent required for mixing with the beneficial agent.

5. The device of claim 1 wherein the means for piercing provides two way fluid communication with the container.

6. The device of claim 1 further comprising:

a plunger operatively attached to the hollow member and capable of being received within the interior of the hollow member and movable into and out of the interior of the hollow member.

7. A method for mixing a beneficial agent housed in a first container with a solution housed in an interior of a second container forming a mixture for administration thereof, the method comprising the steps of:

providing the second container having an upper section with flexible walls and a lower section with rigid walls wherein the upper section is integrally formed with the lower section to form the interior of the second container and further wherein a length of the second container is defined by the integrally formed sections, the length being greater than the width;

providing a means for piercing constructed and arranged to provide selective fluid communication between the first container and the second container wherein the means for piercing is integrally connected to and extends peripherally from the length of the second container;

coupling the second container to the first container with the means for piercing;

compressing the upper section from an exterior of the second container forcing the solution from the second container into the first container; and releasing compression on the upper section of the exterior of the second container allowing the mixture to return to the second container from the first container.

8. The method of claim 7 further comprising the step of:

administering the mixture to a patient.

9. The method of claim 7 wherein the means for piercing extends substantially perpendicularly from a length of the second container.

10. The method of claim 7 further comprising the step of:

mixing the solution and the beneficial agent in the first container.

11. The method of claim 7 wherein only a portion of the solution is compressed from the second container into the first container.

12. A method for drug delivery comprising the steps of:

providing a syringe having an interior for housing a solution, the syringe further having an upper section with flexible walls and a lower section;

coupling a container having an interior containing a beneficial agent to the lower section of the syringe;

establishing fluid communication between the interior of the container and the lower section of the syringe;

compressing a portion of the flexible walls defining the upper section to cause the solution to flow into the container;

releasing compression on the portion of the wall allowing a mixture of the solution and the beneficial agent to return to the interior of the syringe; and coupling a means for administering the mixture in the syringe to a patient.

13. The method of claim 12 wherein the mixture is an individual unit dosage for administering to the patient.

14. The method of claim 12 wherein the lower section of the syringe is substantially rigid.

15. The method of claim 12 wherein the means for administering is a cannula.

16. The method of claim 12 wherein the container is a vial having a re-sealable injection site.

17. The method of claim 12 further comprising the step of:

coupling the syringe to a fluid line for administering the mixture.

* * * * *

UNITED STATES PATENT AND TRADEMARK OFFICE
CERTIFICATE OF CORRECTION

PATENT NO. : 5,484,406
DATED : January 16, 1996
INVENTOR(S) : Joseph Wong, Irwin B. Levine It is certified that error appears in the above-identified patent and that said Letters Patent is hereby corrected as shown below:

At Column 1, line 31, replace "De" with --be--.

At Column 9, line 10, replace "$(D_o-D)D_o$" with --$(D_o-D)/D_o$--.

At Column 11, line 1, replace "25.2" with --252--.

Signed and Sealed this

First Day of June, 1999

Attest:

Q. TODD DICKINSON

*Attesting Officer*

*Acting Commissioner of Patents and Trademarks*